US00PP32129P2

(12) United States Plant Patent
Taliaferro

(10) Patent No.: US PP32,129 P2
(45) Date of Patent: Aug. 25, 2020

(54) TURF BERMUDAGRASS 'JSC 2-21-1'

(50) Latin Name: ***Cynodon dactylon* var. *dactylon* (L.) Pers. x *Cynodon transvaalensis***
Varietal Denomination: JSC 2-21-1

(71) Applicant: JOHNSTON SEED COMPANY, LLC, Enid, OK (US)

(72) Inventor: Charles M. Taliaferro, Stillwater, OK (US)

(73) Assignee: Johnston Seed Company, LLC, Enid, OK (US)

( * ) Notice: Subject to any disclaimer, the term of this patent is extended or adjusted under 35 U.S.C. 154(b) by 0 days.

(21) Appl. No.: 16/501,088

(22) Filed: Feb. 21, 2019

(51) Int. Cl.
*A01H 5/12* (2018.01)

(52) U.S. Cl.
USPC ..... Plt./389

(58) Field of Classification Search
USPC ..... Plt./389
See application file for complete search history.

(56) References Cited

PUBLICATIONS

Parsons et al. 2013 National Turfgrass Evaluation Program Bermudagrass Test:2016 Data. Kansas Agricultural Experiment Station Research Reports vol. 3. Jul. 2017.*

* cited by examiner

*Primary Examiner* — Annette H Para
(74) *Attorney, Agent, or Firm* — Crowe & Dunlevy; Terry L. Watt

(57) ABSTRACT

'JSC 2-21-1' turf bermudagrass is disclosed as a new clonally propagated cultivar. 'JSC 2-21-1' is an interspecific $F_1$ hybrid originating from a cross of *Cynodon dactylon* var. *dactylon* (L.) Pers. x *Cynodon transvaalensis* Burtt-Davy parent plants.

5 Drawing Sheets

SUMMARY OF THE INVENTION

'JSC 2-21-1' turf bermudagrass is disclosed as a new clonally propagated cultivar. 'JSC 2-21-1' is an interspecific $F_1$ hybrid originating from a cross of *Cynodon dactylon* var. *dactylon* (L.) Pers. x *Cynodon transvaalensis* Burtt-Davy parent plants.

DETAILED BOTANICAL DESCRIPTION

Description, Origin and History

'JSC 2-21-1' turf bermudagrass is a clonally propagated interspecific $F_1$ hybrid plant resulting from crossing parent plants of *Cynodon dactylon* var. *dactylon* (L.) Pers. and *Cynodon transvaalensis* (Burtt-Davy). Natural crossing between plants of *Cynodon dactylon* var. *dactylon* and *Cynodon transvaalensis* is known to occur at relatively high frequency. Accordingly, interspecific crossing was achieved by growing a selected plant of *C. dactylon* ('Cda 35-5') in proximity to a selected plant of *C. transvaalensis* ('Ctr 4-10') in a small field plot (ca 9 $m^2$) isolated from other bermudagrass. The plot was located on a Johnston Seed Company (JSC) farm near Enid, Okla. The 'Cda 35-5' and 'Ctr 4-10' plants were selected from JSC bermudagrass breeding nurseries on the bases of good adaptation, turf quality, and fertility. Seeds harvested from the small crossing block in summer 2007 were used to start individual plants in the greenhouse in late winter 2008. These plants were transplanted to a field screening nursery as spaced plants (8' centers, 2' alleys) in May 2008. The screening nursery was located on a JSC farm in Major County Okla. (36° 22' 23.99, −98 21' 25.28) approximately 25 miles west of Enid, Okla. 'JSC 2-21-1' was selected in late 2009 for more comprehensive evaluation. It was identified at time of selection by its nursery plot ID, JSC 2-21-1. It and other JSC experimental turf bermudagrasses were established in a replicated small plot test in May 2010 at the JSC research center at Enid, Okla. This test was managed using the typical protocol used for golf course bermudagrass fairways. Entries in the test were evaluated for visual turf quality and other characteristics influencing overall performance. It was subsequently entered in the National Turf Evaluation Program (NTEP) 2013 bermudagrass test.

Putative chromosome numbers of 'Cda 35-5', 'Ctr 4-10' and 'JSC 2-21-1 are respectively 2n=4x=36, 2n=2x=18, and 2n=3x=27. Accordingly, 'JSC 2-21-1' received 18 chromosomes (2 genomes) from the 'Cda 35-5' parent and 9 chromosomes (1 genome) from the 'Ctr 4-10' parent. 'JSC 2-21-1' is highly sexually sterile, setting only an occasional seed (caryopsis) when grown in the presence of one or more fertile plants of the *C. dactylon* and/or *C. transvaalensis* taxa that serve as pollinators. High sterility is typical for triploid plants with an unbalanced number of genomes. The high sexual sterility of 'JSC 2-21-1' is presumed to result from the nine chromosomes (1 genome) received from 'Ctr 4-10' having no fully homologous chromosomal pairing partners during meiosis. Both parents of 'JSC 2-21-1' are highly sexually fertile. The morphology and sexual sterility of 'JSC 2-21-1' are consistent with expectations for interspecific hybrids of *C. dactylon* and *C. transvaalensis*. The fidelity of 'JSC 2-21-1' has been maintained through many clonal generations of propagation since it's selection in 2008 indicating it to be genetically stable.

Figure 1:
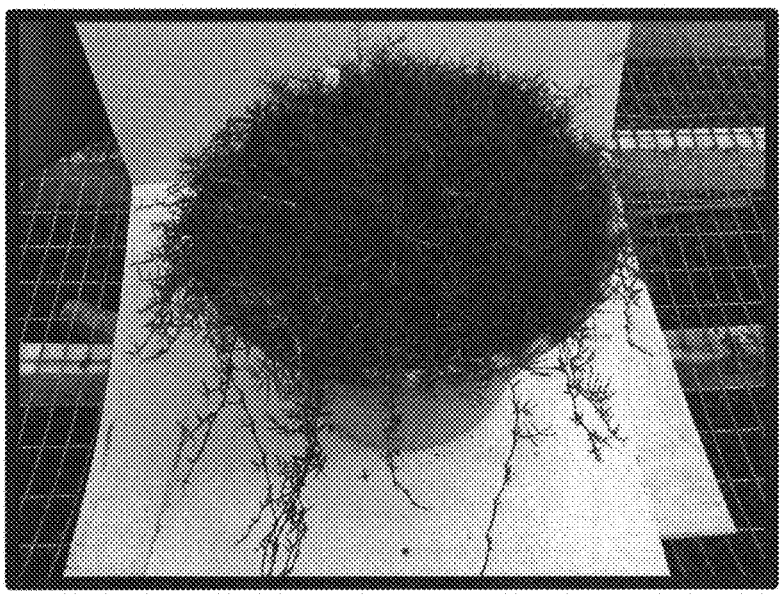
FIG. 1 is a photo of 'JSC 2-21-1' turf bermudagrass growing in a 30 cm pot in the greenhouse.
Figure 2:
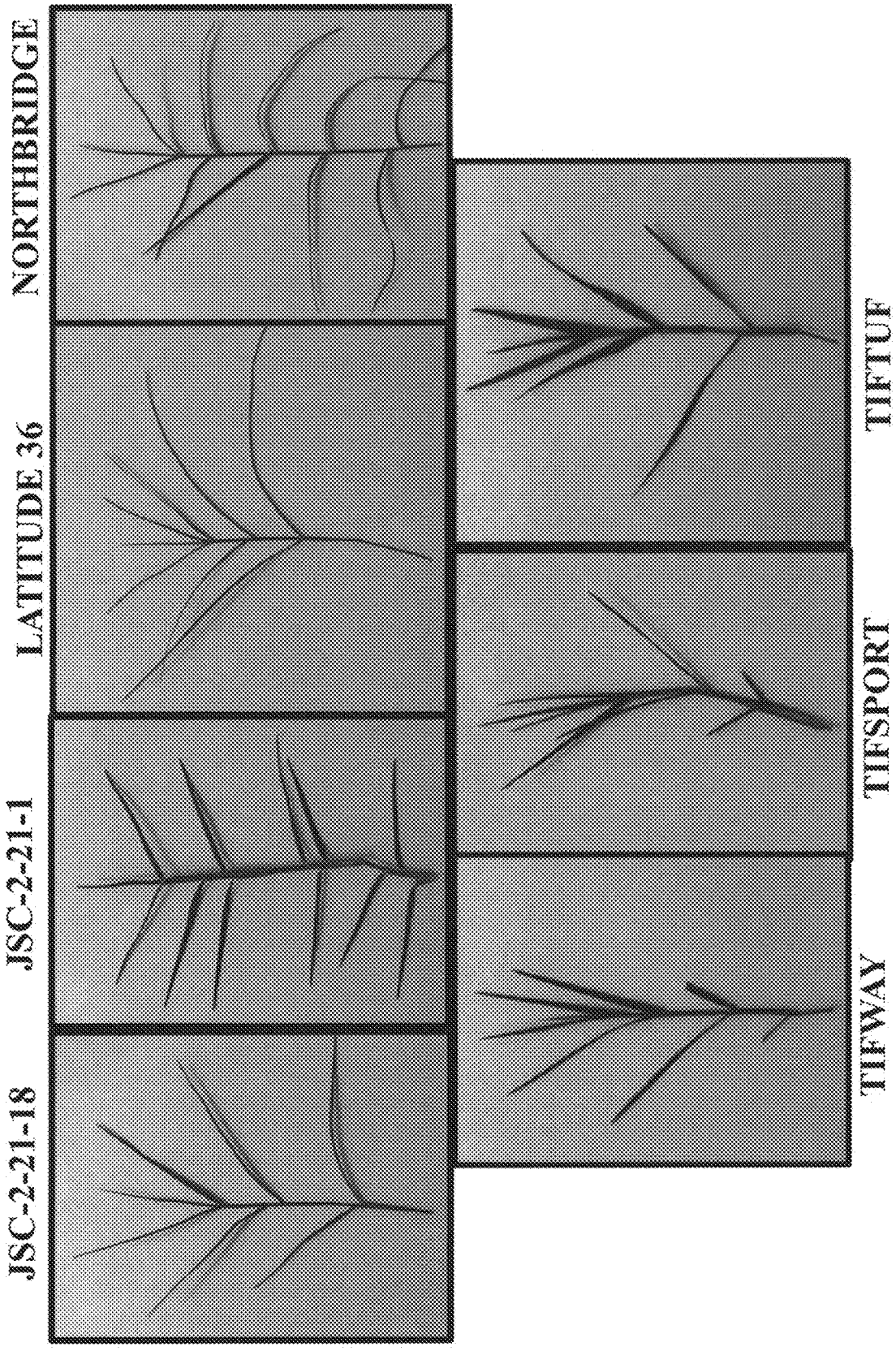
FIG. 2 shows a vegetative shoot of 'JSC 2-21-1' in comparison to vegetative shoots of other turf bermudagrass cultivars.

'JSC 2-21-1' is a stoloniferous sward-forming perennial with slender underground rhizomes. 'JSC 2-21-1 has morphological features with mean values generally between those of the parents. A plant of 'JSC 2-21-1' growing in a greenhouse pot is shown in FIG. 1. A vegetative shoot of 'JSC 2-21-1' is shown in FIG. 2 in comparison to shoots of other turf bermudagrass cultivars. Shoots are slender attaining a maximum height of approximately 20 cm in un-mowed swards. Leaf size (length and width) and stem size (diameter) of JSC '2-21-1' are smaller than 'Cda 35-5' and slightly larger than 'Ctr 4-10'. Shoot density of 'JSC 2-21-1 is high resulting in a dense sward. The sod density (conditioned by shoot density) of 'JSC 2-21-1 is substantially greater than that of 'Cda 35-5' and slightly less than that of 'Ctr 4-10'. 'JSC 2-21-1' leaves are slightly convex, sparsely hirsute on the abaxial and adaxial surfaces, and smooth on the edges. Hairs on the leaves attain a maximum length of approximately 1 mm. Shoots emanating from the $5^{th}$ node of stolons have leaves ($3^{rd}$ from apex) averaging 1.6 mm in width at their base and 28 mm in length (Table 1). The ligule is a membranous rim with short hairs (ca 0.2 mm) on the edge except at the outer edges that have much longer hairs. Leaf sheaths are glabrous.

Figure 3:
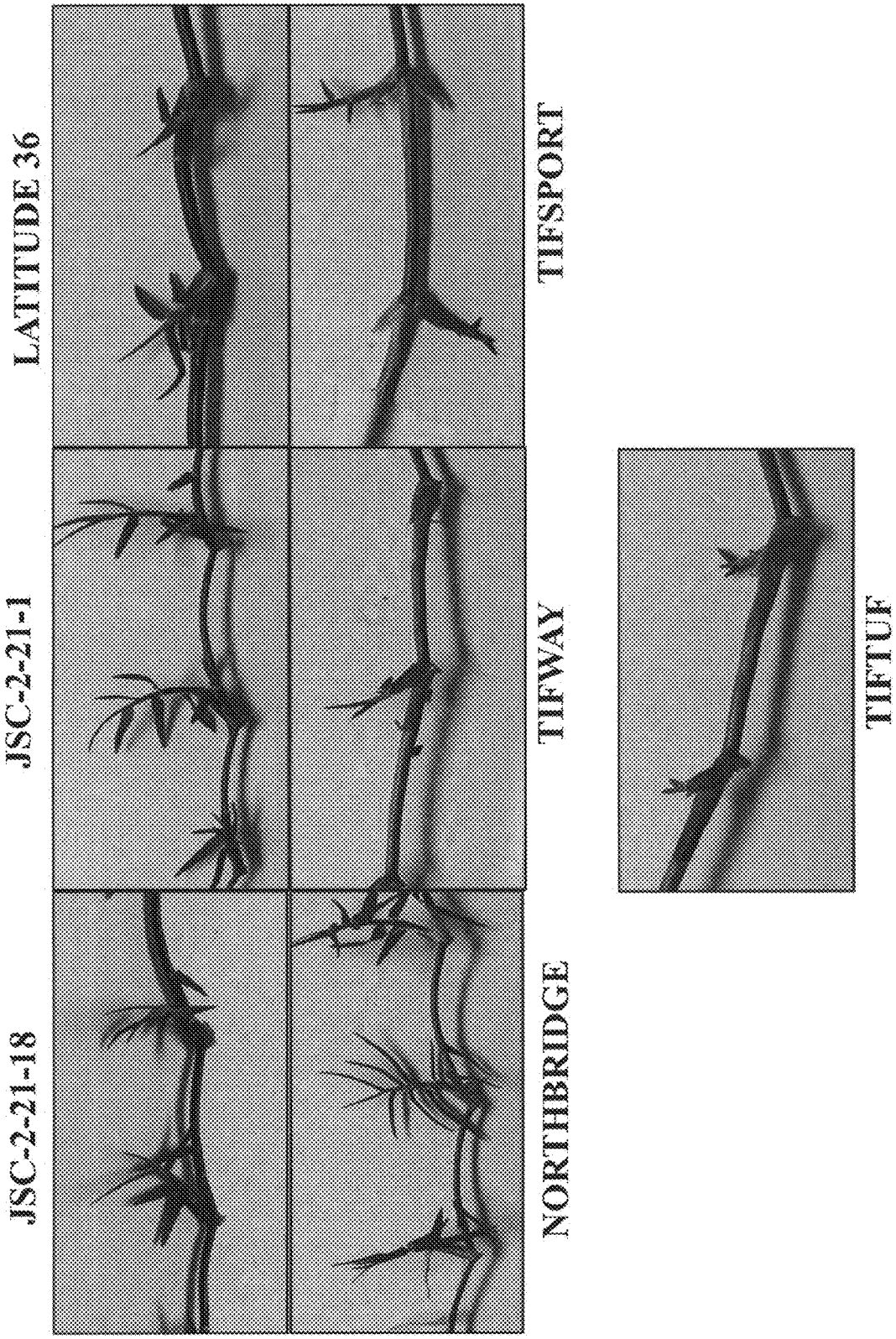
FIG. 3 shows a stolon internode of 'JSC 2-21-1' in comparison to stolon internodes of other turf bermudagrass cultivars.

JSC 2-21-1' stolons are slender with internodes attaining maximum diameter and length of approximately 1 mm and 29 mm, respectively (Table 1). An internode of 'JSC 2-21-1' in comparison to internodes of other turf bermudagrass cultivars are shown in FIG. 3. 'JCC 2-21-1' stolon internodes periodically accumulate anthocyanin pigment in response to environmental conditions and/or developmental stages. The pigment typically results in reddish purple color of the 'JSC 2-21-1' stolon internodes that may vary in intensity through time and growth stages. When assessed on Jun. 26, 2018, 'JSC 2-21-1' internodes were reddish purple in color corresponding to Munsell color 5R 3/4 (Table 1). The color of 'JSC 2-21-1' stolon internodes was judged identical to those of 'JSC 2-21-18' and 'Latitude 36' and only slightly lighter in reddish purple shade than 'Northbridge' stolon internodes which had color corresponding to Munsell color 5R 4/4 (Table 1). Stolon internodes of 'Tifway', 'TifSport' and 'TifTuf' were green in color corresponding to Munsell colors 2.5GY 5/4, 2.5GY 5/4, and 2/5GY 6/6, respectively (FIG. 3, Table 1).

Figure 4:
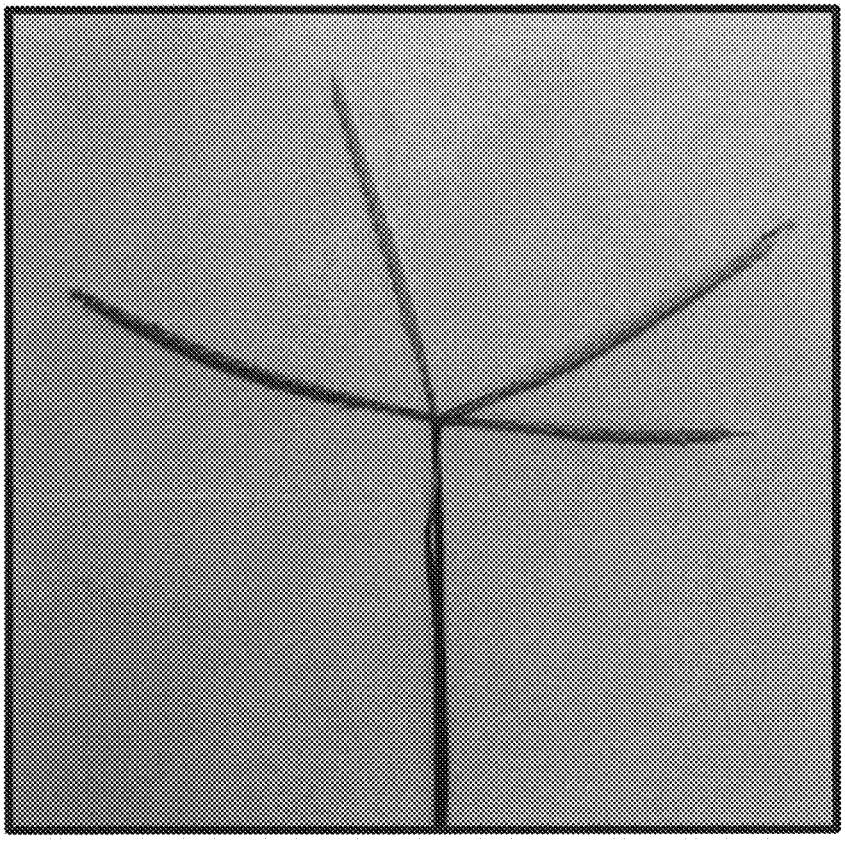
FIG. 4 is a photo of an inflorescence of 'JSC 2-21-1' turf bermudagrass.
Figure 5:
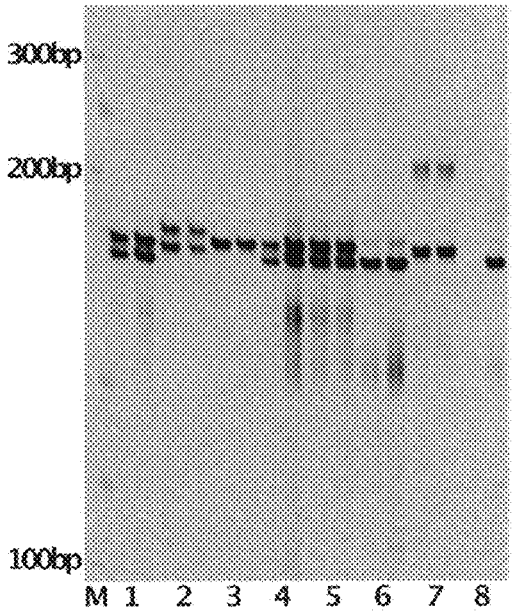
FIG. 5 shows DNA bands amplified in 'JSC 2-21-1' in comparison to seven other clonal turf bermudagrass cultivars by the SSR primer pair CDCA2-181/182. DNA bands were amplified by the SSR primer pair CDCA2-181/182 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 6:
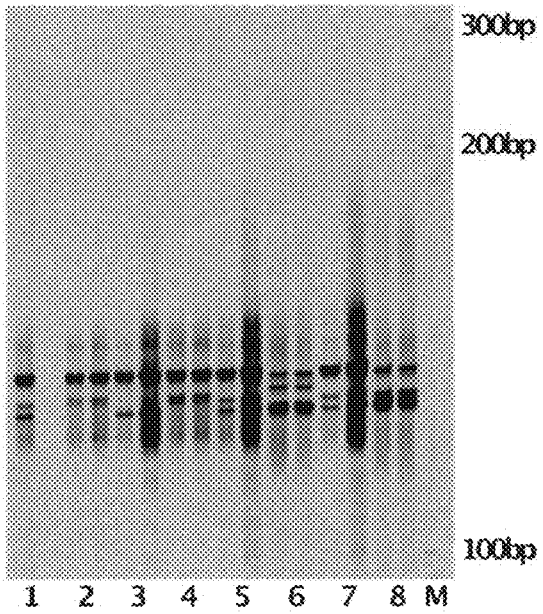
FIG. 6 shows DNA bands amplified in 'JSC 2-21-1' in comparison to seven other clonal turf bermudagrass cultivars by the SSR primer pair CDCA7-615/616. DNA bands were amplified by the SSR primer pair CDCA7-615/616 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 7:
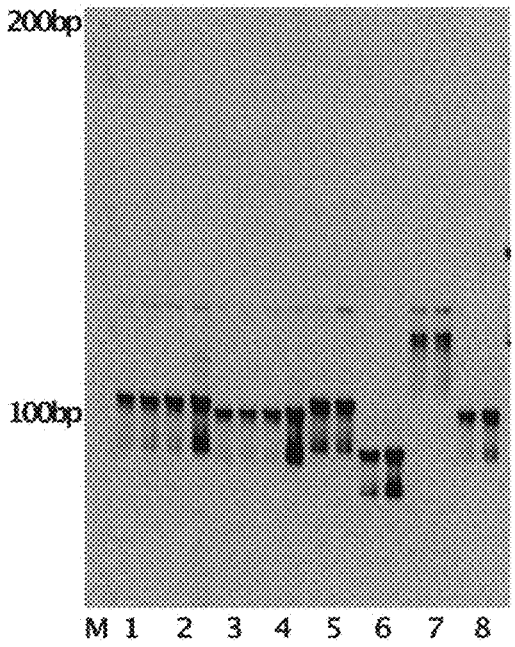
FIG. 7 shows DNA bands amplified in 'JSC 2-21-1' in comparison to seven other clonal turf bermudagrass cultivars by the SSR primer pair CDGA2-1021/1022. DNA bands were amplified by the SSR primer pair CDGA2-1021/1022 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 8:
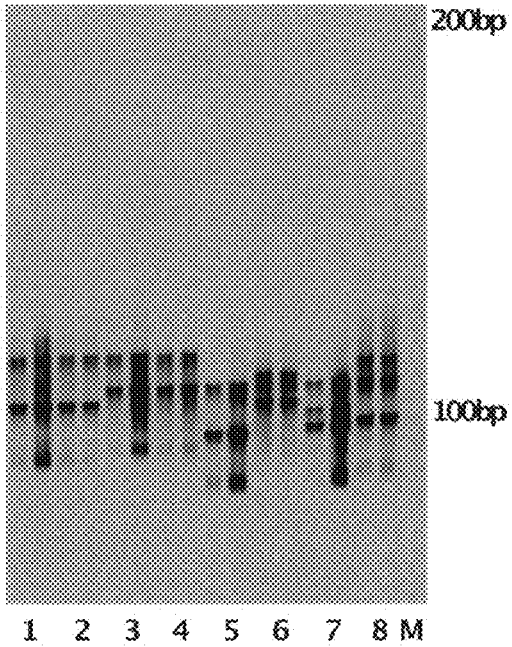
FIG. 8 shows DNA bands amplified in 'JSC 2-21-1' in comparison to seven other clonal turf bermudagrass cultivars by the SSR primer pair CDGA8-1783/1784. DNA bands were amplified by the SSR primer pair CDGA8-1783/1784 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).

Inflorescences of 'JSC 2-21-1' usually have three or four racemes (four in greater frequency than three) arranged in a single whorl (FIG. 4). 'Cda 35-5' and 'Ctr 4-10' parents typically have four and three racemes, respectively, arranged in a single whorl. Racemes of 'JSC 2-21-1' contain about 30 spikelets spaced about 1 mm apart and being approximately 2 mm in length. The lower and upper glumes of 'JSC 2-21-1' spikelets are respectively approximately ⅜th and ¾th the length of the spikelet. Stigma and anther color are purple and yellow, respectively. Anthers contain few, or no, viable pollen grains.

FIGS. 5-8 show DNA profiles of 'JSC 2-21-1' in comparison to seven other clonal turf bermudagrass cultivars. The profiles were generated using four simple sequence repeat (SSR) primer pairs. Each DNA sample had two replicates in PCR. The numbers at the bottom of each figure code for cultivars as follows: 1='JSC 2-20-14', 2='JSC 2-21-1', 3='JSC 2-21-18', 4='Latitude 36', 5='Northbridge', 6='Tifway', 7='Tahoma 31', and 8='TifTuf'. Each code number is centered below the two replicate profiles of each cultivar for each primer pair. The SSR primer pair CDCA2-181/182 (FIG. 5) differentiates 'JSC 2-21-1' from each of the other seven cultivars. The SSR primer pair CDCA7-615/616 (FIG. 6) differentiates 'JSC 2-21-1' from each of the other seven cultivars except 'Latitude 36'. The SSR primer pair CDGA2-1021/1022 (FIG. 7) differentiates 'JSC 2-21-1' from all cultivars except 'JSC 2-20-14' and 'Northbridge'. The SSR primer pair CDGA8-1783/1784 (FIG. 8) differentiates 'JSC 2-21-1' from all cultivars except 'JSC 2-20-14'. Accordingly, the combined SSR profiles confirm the genetic distinctness of 'JSC 2-21-1' in comparison to the other seven cultivars.

Characteristics and Performance

Replicated small plot testing initiated in 2010 by JSC indicated 'JSC 2-21-1' to have overall performance equal to or better than industry standard cultivars included in the test. Specifically, 'JSC 2-21-1' was indicated to be well adapted to the Enid, Okla. (36° 24'2"N 97° 52'51"W) test site and consistently high in visual turf quality. Its good adaptation was evidenced by the absence of winter injury and early green-up in the growing season. Characteristics contributing to its high visual turf quality included fine texture, high shoot density resulting in a uniformly dense sod, and acceptable green color.

Based on JSC test results, 'JSC 2-21-1' was entered in the NTEP 2013 bermudagrass test. The NTEP 2013 bermudagrass test was conducted at 19 test sites in the central and southern United States. The test contained 35 entries encompassing 17 clonal and 18 seed propagated cultivars. The number of test sites reporting data for Progress Reports NTEP 15-2 (2013-14), 16-6 (2015), 17-6 (2016) and 18-12 (2017) were 17, 19, 19, and 19, respectively. Final Report NTEP No. 18-14 was released in December 2018. Details of the test and test results are available at www.ntep.org.

Data from NTEP testing supported JSC data indicating overall high performance of 'JSC 2-21-1'. Tables 2 through 11 contain data extracted from NTEP Reports for 'JSC 2-21-1' and commercial clonal cultivars in the test. The top performing entries in the NTEP test for turf quality and many other traits were clonal cultivars. The high visual turf quality of 'JSC 2-21-1' is evidenced by the results in Table 2. 'JSC 2-21-1' had mean turf quality ratings (TQR) significantly greater than or equal to those of all clonal cultivars except 'TifTuf' in 2014, 2016, and 2017; 'Latitude 36' in 2016 and 2017, and 'Tahoma 31' in 2017. The TQR of 'JSC 2-21-1' were significantly higher than those of 'Astro' in all test years and for the overall mean. The TQR for 'JSC 2-21-1' significantly exceeded those of 'Patriot' and 'Celebration' in four of the test years and for the overall mean. The TQR of 'JSC 2-21-1' was significantly higher than that of 'Tifway' in two of the test years. 'JSC 2-21-1' turf quality ratings (all quality ratings from all locations) were in the top 25% of all cultivars (35 cultivars) for 60% of the test locations.

'JSC 2-21-1' had mean leaf texture ratings (LTR) statistically equal to or greater than all commercial clonal cultivars (Table 3). The LTR for 'JSC 2-21-1' were significantly higher than those of 'Patriot', 'Celebration', and 'Astro' in all test years and for the overall mean. LTR for 'JSC 2-21-1' were significantly higher those of 'Tifway' and 'TifTuf' in two and one test years, respectively. The combined results indicate 'JSC 2-21-1' to have very fine texture consistent with high quality turf bermudagrass cultivars.

Mean NTEP genetic color ratings (GCR) indicate 'JSC 2-21-1' to have lighter green color compared to top performing clonal cultivars for this trait (Table 4). 'Patriot' had GCR for each test year and for overall mean that statistically exceeded the GCR for 'JSC 2-21-1'. 'Celebration' and 'Tifway' had significantly higher GCR than those of 'JSC 2-21-1' in three of the four years and for the overall mean. 'Latitude 36' and 'TifTuf' had GCR significantly greater than those of 'JSC 2-21-1' in two of the four years. 'JSC 2-21-1' had significantly higher GCR than those of 'Astro' in 2014 and 2015. The lighter green color of 'JSC 2-21-1' compared to top rated cultivars for this trait is not expected to significantly limit its use.

Mean NTEP spring green-up ratings (SGR) of 'JSC 2-21-1' were significantly greater than those of 'Tifway', 'Patriot', and 'Celebration' in two of the four years (Table 5). The mean ratings of 'Tahoma 31' in 2014 and 2015 were significantly greater than those of 'JSC 2-21-1'. Other differences between 'JSC 2-21-1' and other cultivars for spring SGR were not statistically significant. Spring green-up is related to winterhardiness conditioned by tolerance to freezing temperatures. The SGR of 'JSC 2-21-1' indicate it to be sufficiently winterhardy for use in the region of the USA where bermudagrass is traditionally grown.

Mean NTEP stand density ratings (SDR) for spring, summer and fall are shown in Tables 6, 7 and 8, respectively. Only the spring SDR for 'TifTuf' in 2014 and 2017 and for 'Latitude 36' in 2014 were significantly greater than those of 'JSC 2-21-1' (Table 6). The spring SDR for 'JSC 2-21-1' were significantly greater than those of 'Celebration' in 2015 and 2016 and those of 'Patriot' and 'Astro' in 2015. The other spring SDR differences between 'JSC 2-21-1' and other cultivars were not significantly different. None of the cultivars had summer SDR significantly greater than those of 'JSC 2-21-1' (Table 7). 'JSC 2-21-1' had mean summer SDR significantly greater than those of 'Celebration' in all four years and for the overall mean. The 'JSC 2-21-1' summer SDR were significantly greater than those of 'Patriot' and 'Astro' in three of the four test years and for the overall mean. The summer SDR of 'JSC 2-21-1' was significantly greater than that of 'Tifway' in 2014. None of the cultivars had fall SDR significantly greater than those of 'JSC 2-21-1' in any test year (Table 8). 'JSC 2-21-1' had fall SDR ratings that were significantly greater than those of 'Patriot' in 2017 and for the overall mean, and significantly greater than those of 'Astro' and 'Celebration' in 2014 and 2016, respectively. The stand density ratings indicate 'JSC 2-21-1' to maintain a dense stand throughout the growing season that is better than or equal to other clonal turf bermudagrass cultivars in the test.

Mean NTEP percent living ground cover ratings (PLGCR) for spring, summer and fall are shown in Tables 9, 10 and 11, respectively. Only 'Tahoma 31' in 2014 had significantly greater spring PLGCR than those of 'JSC 2-21-1' (Table 9). The spring PLGCR of 'JSC 2-21-1' were significantly higher than those of 'Celebration' in three of the test years and for the overall mean. The spring PLGCR of 'JSC 2-21-1' were significantly higher than those of 'Tifway' in two of the test years, and significantly higher than those of 'Latitude 36' and 'Patriot' in 2015 and 2017, respectively. Only 'TifTuf' in 2017 had a significantly higher PLGCR than that of 'JSC 2-21-1' (Table 10). 'JSC 2-21-1' had significantly higher summer PLGCR than those of 'Latitude 36', 'Tifway' and 'Celebration' in two of the four test years and for the 4-year mean. The summer PLGCR of 'JSC 2-21-1' was significantly higher than that of 'Patriot' in 2016. None of the cultivars had significantly higher fall PLGCR than 'JSC 2-21-1' in any test year or for the overall mean (Table 11). 'JSC 2-21-1' had significantly higher fall PLGCR than those of 'Tifway' and 'Celebration' in 2014 and 'Patriot' in 2017. The PLGCR indicate 'JSC 2-21-1' to have high percentages of living ground cover through the growing season that are consistent with expectations for high quality turf.

Summary Comparative Performance. Available test data indicate 'JSC 2-21-1' to be highly competitive in performance with other commercial clonal turf bermudagrass cultivars. The data indicate it to be well adapted to the traditional geographic region in the USA where turf bermudagrass is grown. Its good cold tolerance reduces risk of winter injury compared to many turf bermudagrass cultivars, particularly when grown in the region of transition between warm- and cool-season grass species. It has consistently demonstrated high visual turf quality due primarily to its very fine texture and maintenance of an attractive uniform dense stand (sod) throughout the growing season.

TABLE 1

Stolon internode length, diameter and Munsell Color Chart ratings and leaf length and width of seven turf bermudagrass cultivars growing in greenhouse pots Jun. 26, 2018.[1]

| | Internode | | | Leaf | |
|---|---|---|---|---|---|
| Cultivar | Length | Diameter mm | Munsell[3] H V/C | Length | Width mm |
| JSC 2-21-1 | 29.25 ab[2] | 1.24 bc | 5R 3/4 | 28.20 b | 1.57 c |
| JSC 2-21-18 | 24.76 ab | 1.06 c | 5R 3/4 | 20.02 b | 1.61 c |
| Latitude 36 | 25.81 ab | 1.15 be | 5R 3/4 | 18.97 b | 1.66 bc |
| Northbridge | 30.54 a | 1.32 b | 5R 4/4 | 29.30 ab | 1.95 ab |
| Tifway | 24.40 ab | 1.30 a | 2.5 GY 5/4 | 39.23 a | 1.65 bc |
| Tifsport | 21.06 b | 1.34 b | 2.5 GY 5/4 | 21.06 b | 1.34 c |
| Tiftuf | 27.57 ab | 1.62 a | 2.5 GY 6/6 | 26.80 b | 2.04 a |
| Mean | 26.20 | 1.29 | 26.23 | 1.69 | |
| Statistical Sig.[4] | * | ** | | ** | ** |

[1]Each cultivar was grown in one 30 cm diameter pot in a greenhouse. Stolons of each cultivar were allowed to grow over the edges of the pots and attain lengths up to about 30 cm. Measurements were made on the 5th internode from the apex of ten respective stolons per cultivar. Leaf measurements were from leaves emanating from the subtending node, with length being from the collar to the apex and width being taken near the leaf base.
[2]Means in the same column followed by the same letter are not significantly different as indicated by Tukeys's Honest Significant Difference Test (P = 0.05).
[3]Munsell Color Charts for Plant Tissues, GretagMacbeth LLC, 617 Little Britain Road, New Windsor, NY 12553-6148. H V/C = Hue Value/Chroma
[4]*, ** Means are significantly different at the 0.05 and 0.01 probability levels, respectively.

TABLE 2

Turfgrass quality ratings and maximum in top 25 percent for 'JSC 2-21-1' and commercial vegetative cultivars in the National Turfgrass Evaluation Program (NTEP) 2013 bermudagrass test.

| | Year[1] | | | | | 5-Yr Summary[2] | |
|---|---|---|---|---|---|---|---|
| Cultivar | 2013 | 2014 | 2015 | 2016 | 2017 | Mean | Maximum[3] |
| | Turfgrass quality ratings 1-9, 9 = ideal turf | | | | | | |
| Tiffuf (DT-1) | 6.5 | 6.6 | 6.7 | 6.8 | 6.9 | 6.7 | 93.3 |
| Tahoma 31 (OKC 1131) | 6.5 | 6.5 | 6.6 | 6.6 | 6.8 | 6.6 | 73.3 |
| Latitude 36 | 6.3 | 6.4 | 6.3 | 6.7 | 6.7 | 6.6 | 66.7 |
| JSC 2-21-1 | 6.3 | 6.3 | 6.5 | 6.4 | 6.4 | 6.4 | 60.0 |
| Tifway | 6.0 | 5.9 | 5.8 | 6.5 | 6.6 | 6.3 | 46.7 |
| Patriot | 5.9 | 6.0 | 6.1 | 6.3 | 6.3 | 6.2 | 46.7 |
| Astro | 5.8 | 5.8 | 6.0 | 6.2 | 6.0 | 6.0 | 6.7 |
| Celebration | 6.1 | 5.5 | 5.2 | 5.8 | 5.8 | 5.7 | 13.3 |
| LSD Value[4] | 0.3 | 0.2 | 0.2 | 0.2 | 0.2 | 0.3 | |
| C.V.[5] | 6.9 | 9.7 | 8.1 | 7.3 | 8.3 | 7.3 | |

[1]Data are from appendix tables in NTEP Progress Reports 15-2 (2013-2014), 16-6 (2015), 17-6 (2016), and 18-12 (2017).
[2]Data are from the appendix table in NTEP Final Report 18-4.
[3]The percentage of locations where that entry finished in the top 25% of all entries (35 total entries).
[4]To determine statistical differences among cultivars within a column, subtract one entry's mean from another entry's mean. Statistical difference occurs when this value is larger than the corresponding Least Significant Difference (LSD 0.05) value.
[5]C.V. (coefficient of variation) indicates the percent variation of the mean in each column.

TABLE 3

Leaf texture ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2013-14 | 2015 | 2016 | 2017 | Mean[2] |
| | Leaf texture ratings 1-9, 9 = very fine | | | | |
| Latitude 36 | 7.6 | 6.7 | 6.5 | 6.8 | 6.4 |
| JSC 2-21-1 | 7.6 | 6.4 | 6.5 | 6.6 | 6.1 |
| Tahoma 31 (OKC 1131) | 7.4 | 6.5 | 6.4 | 6.7 | 6.1 |

TABLE 3-continued

Leaf texture ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2013-14 | 2015 | 2016 | 2017 | Mean[2] |
| | Leaf texture ratings 1-9, 9 = very fine | | | | |
| Tifway | 7.3 | 6.0 | 6.0 | 6.6 | 6.0 |
| TifTuf (DT-1) | 7.1 | 6.3 | 6.3 | 6.6 | 5.9 |
| Patriot | 6.5 | 6.0 | 5.6 | 5.7 | 5.2 |
| Astro | 6.2 | 5.5 | 5.2 | 5.6 | 5.1 |
| Celebration | 6.1 | 5.3 | 5.3 | 5.5 | 4.9 |
| LSD Value[3] | 0.3 | 0.3 | 0.4 | 0.3 | 0.5 |
| C.V.[4] | 8.7 | 9.4 | 10.7 | 8.7 | 11.7 |

[1]Data are from NTEP Progress Reports 15-2 (2013-2014), Table 11C; 16-6 (2015), Table 22C; 17-6 (2016), Table 11C; and 18-12 (2017), Table 9C.
[2]Data are from Final Report NTEP No. 18-4, Table 9C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 4

Genetic color ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Genetic color ratings 1-9, 9 = dark green | | | | |
| Patriot | 7.4 | 7.2 | 7.7 | 7.5 | 7.4 |
| Celebration | 7.7 | 6.6 | 7.2 | 7.3 | 7.1 |
| Tifway | 7.6 | 6.7 | 7.4 | 6.8 | 7.1 |
| Tahoma 31 (OKC 1131) | 7.2 | 7.1 | 7.1 | 6.7 | 6.9 |
| TifTuf (DT-1) | 7.1 | 6.6 | 6.9 | 6.2 | 6.7 |
| Latitude 36 | 7.1 | 6.7 | 6.7 | 6.4 | 6.6 |
| JSC 2-21-1 | 6.7 | 6.3 | 6.4 | 6.0 | 6.5 |
| Astro | 6.3 | 5.7 | 6.2 | 5.9 | 6.3 |
| LSD Value[3] | 0.3 | 0.4 | 0.3 | 0.3 | 0.5 |
| C.V.[4] | 10.1 | 13.7 | 8.3 | 10.7 | 10.7 |

[1]Data are from NTEP Progress Reports 15-2 (2013-2014), Table 9C; 16-6 (2015), Table 20C; 17-6 (2016), Table 9C; and 18-12 (2017), Table 1C.
[2]Data are from Final Report NTEP No. 18-4, Table 7C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 5

Spring green-up ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Spring green-up ratings 1-9, 9 = completely green | | | | |
| Tahoma 31 (OKC 1131) | 6.1 | 6.0 | 5.3 | 6.0 | 5.7 |
| Astro | 5.1 | 5.4 | 5.6 | 5.7 | 5.5 |
| TifTuf (DT-1) | 5.2 | 5.6 | 5.3 | 6.1 | 5.3 |
| JSC 2-21-1 | 5.4 | 5.3 | 5.2 | 5.9 | 5.0 |
| Latitude 36 | 5.3 | 5.4 | 5.5 | 6.0 | 4.9 |
| Patriot | 4.8 | 4.5 | 4.9 | 5.2 | 4.8 |
| Tifway | 4.1 | 4.7 | 4.8 | 5.3 | 4.5 |

TABLE 5-continued

Spring green-up ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Spring green-up ratings 1-9, 9 = completely green | | | | |
| Celebration | 3.7 | 4.5 | 4.9 | 4.7 | 4.4 |
| LSD Value[3] | 0.4 | 0.5 | 0.5 | 0.5 | 0.7 |
| C.V.[4] | 18.5 | 19.9 | 17.6 | 18.1 | 20.8 |

[1]Data are from NTEP Progress Reports 15-2 (2013-2014), Table 10C; 16-6 (2015), Table 21C; 17-6 (2016), Table 10C; and 18-12 (2017), Table 8C.
[2]Data are from Final Report NTEP No. 18-4, Table 8C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 6

Spring density ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Spring density ratings 1-9, 9 = maximum density | | | | |
| TifTuf (DT-1) | 7.1 | 6.9 | 5.8 | 6.9 | 6.8 |
| Latitude 36 | 7.0 | 6.8 | 6.7 | 6.2 | 6.8 |
| Tifway | 6.9 | 6.8 | 5.8 | 6.1 | 6.6 |
| JSC 2-21-1 | 6.3 | 7.0 | 6.0 | 5.9 | 6.4 |
| Tahoma 31 (OKC 1131) | 6.3 | 7.1 | 5.7 | 5.9 | 6.4 |
| Patriot | 6.3 | 6.3 | 6.2 | 5.6 | 6.1 |
| Astro | 6.3 | 6.3 | 6.0 | 5.6 | 6.1 |
| Celebration | 6.6 | 5.5 | 4.8 | 6.0 | 6.0 |
| LSD Value[1] | 0.6 | 0.5 | 0.9 | 0.8 | 0.6 |
| C.V.[4] | 9.4 | 10.4 | 13.9 | 14.2 | 11.9 |

[1]Data are from NTEP Progress Reports 15-2 (2013-2014), Table 13C; 16-6 (2015), Table 23C; 17-6 (2016), Table 12C; and 18-12 (2017), Table 10C.
[2]Data are from Final Report NTEP No. 18-4, Table 11C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 7

Summer density ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Summer density ratings 1-9, 9 = maximum density | | | | |
| Latitude 36 | 7.6 | 7.3 | 6.8 | 7.3 | 7.4 |
| TifTuf (DT-1) | 7.7 | 7.4 | 6.9 | 7.4 | 7.4 |
| Tahoma 31 (OKC 1131) | 7.5 | 7.2 | 7.0 | 7.3 | 7.4 |
| JSC 2-21-1 | 7.6 | 7.3 | 7.0 | 7.1 | 7.3 |
| Tifway | 7.2 | 7.1 | 7.1 | 7.1 | 7.2 |
| Patriot | 6.9 | 6.7 | 6.6 | 6.4 | 6.7 |
| Celebration | 6.3 | 6.3 | 6.3 | 6.5 | 6.5 |
| Astro | 6.5 | 6.5 | 6.7 | 6.2 | 6.5 |

TABLE 7-continued

Summer density ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Summer density ratings 1-9, 9 = maximum density | | | | |
| LSD Valuej | 0.4 | 0.4 | 0.5 | 0.5 | 0.4 |
| C.V.[4] | 8.3 | 7.3 | 10.5 | 10.4 | 9.1 |

[1]Data are from NTEP Progress Reports 15-2 (2013-2014), Table 14C; 16-6 (2015), Table 24C; 17-6 (2016), Table 13C; and 18-12 (2017), Table 11C.
[2]Data are from Final Report NTEP No. 18-4, Table 12C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 8

Fall density ratings for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Fall density ratings 1-9, 9 = maximum density | | | | |
| TifTuf(DT-l) | 7.7 | 7.3 | 7.8 | 7.5 | 7.6 |
| Tifway | 7.4 | 7.1 | 7.2 | 7.4 | 7.3 |
| Latitude 36 | 7.5 | 7.3 | 7.0 | 7.1 | 7.3 |
| Tahoma 31 (OKC 1131) | 7.7 | 7.3 | 6.7 | 7.3 | 7.3 |
| JSC 2-21-1 | 7.3 | 7.0 | 7.2 | 6.9 | 7.1 |
| Celebration | 7.1 | 6.9 | 6.3 | 6.7 | 6.8 |
| Astro | 6.4 | 6.5 | 6.5 | 6.5 | 6.5 |
| Patriot | 6.8 | 6.7 | 7.0 | 5.9 | 6.4 |
| LSD Value[3] | 0.5 | 0.5 | 0.8 | 0.6 | 0.6 |
| C.V.[4] | 8.8 | 10.2 | 10.5 | 12.6 | 10.8 |

[1]Data are from NTEP Progress Reports 15-2 (2013-2014), Table 15C; 16-6 (2015), Table 25C; 17-6 (2016), Table 14C; and 18-12 (2017), Table 12C.
[2]Data are from Final Report NTEP No. 18-4, Table 13C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 9

Percent living ground cover ratings (spring) for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | % ground cover rating | | | | |
| Tahoma 31 (OKC 1131) | 79.9 | 89.2 | 95.5 | 89.4 | 88.0 |
| TifTuf (DT-1) | 70.6 | 87.9 | 95.3 | 92.4 | 86.6 |
| JSC 2-21-1 | 66.8 | 87.2 | 94.9 | 89.4 | 84.8 |
| Astro | 68.6 | 84.9 | 95.2 | 89.6 | 83.6 |
| Latitude 36 | 58.2 | 78.3 | 96.4 | 90.5 | 80.7 |
| Patriot | 70.2 | 79.5 | 92.3 | 81.1 | 80.4 |
| Tifway | 56.1 | 68.8 | 93.8 | 86.6 | 77.9 |
| Celebration | 59.8 | 66.6 | 85.3 | 79.1 | 75.0 |

TABLE 9-continued

Percent living ground cover ratings (spring) for 'JSC 2-21-1' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| LSD Value[3] | 9.5 | 8.0 | 4.9 | 4.9 | 7.8 |
| C.V.[4] | 24.4 | 16.1 | 6.6 | 8.4 | 13.6 |

[1]Data are from NTEP Progress Reports 15-2 (2013-2014), Table 16C; 16-6 (2015), Table 26C; 17-6 (2016), Table 15C; and 18-12(2017), Table 13C.
[2]Data are from Final Report NTEP No. 18-4, Table 14C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 10

Percent living ground cover ratings (summer) for 'JSC 2-21-1' and commercial vegetative bermudagrass cultivars in the National Turfgrass Evaluation Program 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| TifTuf (DT-1) | 89.9 | 96.9 | 95.9 | 97.0 | 95.3 |
| Tahoma 31 (OKC 1131) | 90.1 | 96.6 | 95.9 | 93.5 | 94.7 |
| Astro | 89.1 | 96.1 | 97.3 | 91.4 | 94.3 |
| JSC 2-21-1 | 84.6 | 96.2 | 96.1 | 92.4 | 93.4 |
| Patriot | 82.4 | 92.1 | 91.3 | 92.5 | 90.6 |
| Latitude 36 | 72.9 | 84.5 | 95.2 | 95.4 | 88.9 |
| Tifway | 76.2 | 78.4 | 95.8 | 96.1 | 88.8 |
| Celebration | 75.6 | 77.8 | 95.8 | 94.4 | 88.3 |

TABLE 10-continued

Percent living ground cover ratings (summer) for 'JSC 2-21-1'

| | | | | | |
|---|---|---|---|---|---|
| LSD Value[3] | 5.8 | 6.0 | 2.4 | 3.4 | 4.2 |
| C.V.[4] | 10.9 | 9.5 | 3.2 | 5.0 | 6.1 |

[1]Data are from NTEP Progress Reports 15-2 (2013-2014), Table 17C; 16-6 (2015), Table 27C; 17-6 (2016), Table 16C; and 18-12 (2017), Table 14C.
[2]Data are from Final Report NTEP No. 18-4, Table 15C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 11

Percent living ground cover ratings (fall) for 'JSC 2-21-1' and commercial vegetative bermudagrass cultivars in the National Turfgrass Evaluation Program 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| Astro | 96.2 | 98.8 | 96.3 | 91.3 | 95.1 |
| TifTuf(DT-l) | 95.1 | 98.8 | 95.9 | 94.6 | 95.1 |
| Tahoma 31 (OKC 1131) | 96.3 | 98.7 | 94.6 | 93.0 | 94.3 |
| JSC 2-21-1 | 92.7 | 98.9 | 95.5 | 91.7 | 93.6 |
| Latitude 36 | 91.5 | 98.5 | 94.5 | 91.5 | 92.8 |
| Celebration | 84.9 | 98.5 | 95.4 | 91.4 | 92.2 |
| Patriot | 96.4 | 97.3 | 94.2 | 85.2 | 92.0 |
| Tifsvay | 81.2 | 98.4 | 94.4 | 94.0 | 91.0 |
| LSD Value[3] | 4.8 | 1.7 | 2.2 | 3.6 | 3.8 |
| C.V.[4] | 8.1 | 2.4 | 2.8 | 6.0 | 4.7 |

[1]Data are from NTEP Progress Reports 15-2 (2013-2014), Table 18C; 16-6 (2015), Table 28C; 17-6 (2016), Table 17C; and 18-12 (2017), Table 15C.
[2]Data are from Final Report NTEP No. 18-4, Table 16C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

I claim:

1. A turf clonal bermudagrass cultivar substantially as described and illustrated in the specification herein.

* * * * *